(12) United States Patent
Huang

(10) Patent No.: US 9,653,338 B2
(45) Date of Patent: May 16, 2017

(54) SYSTEM AND METHOD FOR NON-CONTACT WAFER CHUCKING

(71) Applicant: KLA-Tencor Corporation, Milpitas, CA (US)

(72) Inventor: Luping Huang, Dublin, CA (US)

(73) Assignee: KLA-Tencor Corporation, Milpitas, CA (US)

(*) Notice: Subject to any disclaimer, the term of this patent is extended or adjusted under 35 U.S.C. 154(b) by 47 days.

(21) Appl. No.: 14/571,000

(22) Filed: Dec. 15, 2014

(65) Prior Publication Data

US 2015/0179495 A1    Jun. 25, 2015

Related U.S. Application Data

(60) Provisional application No. 61/920,456, filed on Dec. 23, 2013.

(51) Int. Cl.
  *G01N 21/00* (2006.01)
  *H01L 21/683* (2006.01)
  (Continued)

(52) U.S. Cl.
  CPC ..... *H01L 21/6838* (2013.01); *G01N 21/9503* (2013.01); *H01L 21/68728* (2013.01);
  (Continued)

(58) Field of Classification Search
  CPC .......... H01L 21/6838; H01L 21/68728; H01L 21/306; H01L 21/67051; G01N 21/9503;
  (Continued)

(56) References Cited

U.S. PATENT DOCUMENTS 3,523,706 A    8/1970   Logue
5,805,278 A    9/1998   Danko
            (Continued)

FOREIGN PATENT DOCUMENTS

DE    202004011907    12/2004
WO    2006072422    7/2006
WO    2008037791 A1    4/2008

OTHER PUBLICATIONS

PCT Search Report, Application No. PCT/US2014/071478, Mail Date Apr. 13. 2015.

*Primary Examiner* — Tarifur Chowdhury
*Assistant Examiner* — Isiaka Akanbi
(74) *Attorney, Agent, or Firm* — Sulter Swantz pc llo

(57) ABSTRACT

A non-contact wafer chucking apparatus includes a wafer chuck and a gripper assembly coupled to a portion of the wafer chuck. The wafer chuck includes pressurized gas elements configured to generate pressurized gas regions across a surface of the wafer chuck suitable for elevating the wafer above the surface of the wafer chuck. The wafer chuck further includes vacuum elements configured to generate reduced pressure regions across the surface of the wafer chuck having a pressure lower than the pressurized gas regions. The reduced pressure regions are suitable for securing the wafer above the wafer chuck without contact to the wafer chuck. The chucking apparatus includes a rotational drive unit configured to selectively rotate the wafer chuck. The gripper elements are reversibly couplable to an edge portion of the wafer so as to secure the wafer such that the wafer and gripper assembly rotate synchronously with the wafer chuck.

37 Claims, 9 Drawing Sheets

(51) Int. Cl.
 *G01N 21/95*    (2006.01)
 *H01L 21/687*   (2006.01)
 *G01N 21/84*    (2006.01)

(52) U.S. Cl.
 CPC . *G01N 2021/8461* (2013.01); *Y10T 29/49998* (2015.01); *Y10T 279/11* (2015.01)

(58) Field of Classification Search
 CPC .......... G01N 2021/8461; Y10T 279/11; Y10T 29/49998
 USPC ............................................ 356/237.2–237.6
 See application file for complete search history.

(56) References Cited

U.S. PATENT DOCUMENTS

| | | | |
|---|---|---|---|
| 6,160,615 A * | 12/2000 | Matsui | H01L 21/67288 356/237.4 |
| 6,621,570 B1 | 9/2003 | Danko | |
| 6,702,302 B2 * | 3/2004 | Smedt | B25B 5/06 118/503 |
| 7,055,535 B2 * | 6/2006 | Kunisawa | H01L 21/6838 134/157 |
| 7,092,082 B1 | 8/2006 | Dardzinski | |
| 7,284,760 B2 | 10/2007 | Siebert et al. | |
| 7,374,391 B2 | 5/2008 | Rice et al. | |
| 7,682,933 B1 | 3/2010 | Loomis | |
| 8,444,126 B2 | 5/2013 | Siebert et al. | |
| 8,616,598 B2 | 12/2013 | Cadee et al. | |
| 2002/0153676 A1 * | 10/2002 | Noguchi | H01L 21/67288 279/106 |
| 2007/0175863 A1 * | 8/2007 | Koyata | H01L 21/02019 216/84 |
| 2008/0229811 A1 | 9/2008 | Zhao et al. | |
| 2010/0001449 A1 | 1/2010 | Siebert et al. | |
| 2011/0069313 A1 | 3/2011 | Sakai et al. | |
| 2013/0309874 A1 | 11/2013 | Kinoshita et al. | |

\* cited by examiner

SYSTEM AND METHOD FOR NON-CONTACT WAFER CHUCKING

CROSS-REFERENCE TO RELATED APPLICATION

The present application claims the benefit under 35 U.S.C. §119(e) of U.S. Provisional Application Ser. No. 61/920,456, filed Dec. 23, 2013, entitled WAFER EDGE GRIPPING CHUCK MECHANISM WITHOUT CONTACT ON BACK SIDE, naming Luping Huang as an inventor, which is incorporated herein by reference in the entirety.

TECHNICAL FIELD

The present invention generally relates to a wafer chuck for use in a wafer characterization system and, in particular, to a non-contact wafer chuck.

BACKGROUND

As tolerances on semiconductor device fabrication processes continue to narrow, the demand for improved semiconductor wafer review tools continues to increase. One such review tool includes a wafer inspection tool, such as a wafer edge inspection tool. In such an optical system, an associated wafer chuck may be used to rotate the wafer during edge inspection. Some wafer chucks may provide an air bearing that elevates the wafer above the wafer chuck surface. Such systems, however, suffer from height variations associated with the wafer chuck as the wafer is rotated with respect to the underlying wafer chuck. Therefore, it would be advantageous to provide a system and method that cures the defects identified in the previous art.

SUMMARY

An apparatus for non-contact chucking a wafer is disclosed, in accordance with an illustrative embodiment of the present invention. In one illustrative embodiment, the apparatus includes a wafer chuck. In one illustrative embodiment, the wafer chuck includes one or more pressurized gas elements configured to generate one or more pressurized gas regions across a surface of the wafer chuck suitable for elevating the wafer above the surface of the wafer chuck. In another illustrative embodiment, the wafer chuck further includes one or more vacuum elements configured to generate one or more reduced pressure regions across the surface of the wafer chuck. In one illustrative embodiment, the reduced pressure regions have a pressure lower than the pressurized gas regions. In another illustrative embodiment, the one or more reduced pressure regions are suitable for securing the wafer above the wafer chuck without contact to the wafer chuck. In another illustrative embodiment, the apparatus includes a gripper assembly coupled to a portion of the wafer chuck. In another illustrative embodiment, the apparatus includes a rotational drive unit mechanically coupled to the wafer chuck. In another illustrative embodiment, the rotational drive unit is configured to selectively rotate the wafer chuck. In another illustrative embodiment, the gripper assembly is reversibly couplable to one or more edge portions of the wafer so as to laterally secure the wafer such that the wafer and the gripper assembly rotate synchronously with the wafer chuck during rotation of the wafer chuck by the rotational drive unit.

An optical system is disclosed, in accordance with an illustrative embodiment of the present invention. In one illustrative embodiment, the optical system includes a wafer chucking sub-system. In another illustrative embodiment, the optical system includes an illumination source configured to illuminate one or more portions of the wafer secured by the wafer chucking sub-system. In another illustrative embodiment, the optical system includes a detector configured to collect illumination from the illuminated one or more portions of the wafer. In one illustrative embodiment, wafer chucking sub-system includes a wafer chuck. In one illustrative embodiment, the wafer chuck includes one or more pressurized gas elements configured to generate one or more pressurized gas regions across a surface of the wafer chuck suitable for elevating the wafer above the surface of the wafer chuck. In another illustrative embodiment, the wafer chuck further includes one or more vacuum elements configured to generate one or more reduced pressure regions across the surface of the wafer chuck. In one illustrative embodiment, the reduced pressure regions have a pressure lower than the pressurized gas regions. In another illustrative embodiment, the one or more reduced pressure regions are suitable for securing the wafer above the wafer chuck without contact to the wafer chuck. In another illustrative embodiment, the wafer chucking sub-system includes a gripper assembly coupled to a portion of the wafer chuck. In another illustrative embodiment, the wafer chucking sub-system includes a rotational drive unit mechanically coupled to the wafer chuck. In another illustrative embodiment, the rotational drive unit is configured to selectively rotate the wafer chuck. In another illustrative embodiment, the gripper assembly is reversibly couplable to one or more edge portions of the wafer so as to laterally secure the wafer such that the wafer and the gripper assembly rotate synchronously with the wafer chuck during rotation of the wafer chuck by the rotational drive unit.

An apparatus for non-contact chucking of a wafer is disclosed, in accordance with an illustrative embodiment of the present invention. In one illustrative embodiment, the method includes generating one or more pressurized gas regions across a surface of a wafer chuck in order to elevate the wafer above the surface of the wafer chuck. In another illustrative embodiment, the method includes generating one or more reduced pressure regions across the surface of the wafer chuck in order to secure the wafer above the wafer chuck without contact to the wafer chuck. In another illustrative embodiment, the method includes reversibly coupling a gripper assembly to an edge portion of the wafer in order to rotationally secure the wafer with respect to the wafer chuck. In another illustrative embodiment, the method includes synchronously rotating the wafer, gripper assembly and the wafer chuck at a selected rotational velocity.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 4, a system and method for non-contact chucking of a wafer is described in accordance with the present disclosure. The use of a non-contact wafer chuck is described generally in U.S. Pat. No. 8,444,126 to Siebert et al., issued on May 21, 2013, which is incorporated herein by reference in the entirety.

Embodiments of the present disclosure are directed to a wafer chuck and gripping device suitable for elevating and securing a wafer, such as a semiconductor wafer (e.g., 200 to 500 mm wafer), above the wafer chuck. Embodiments of the present disclosure are further directed to rotating the wafer and wafer chuck synchronously such that during a given scan there is no relative emotion between the wafer and the wafer chuck. Such a configuration aids in avoiding scanning errors caused by height variation and vibration of the wafer chuck. It is further noted that the wafer chucking system of the present disclosure may be implemented in a variety of optical measurement contexts, such as, but not limited to, a wafer edge inspection system.

Figure 1A:
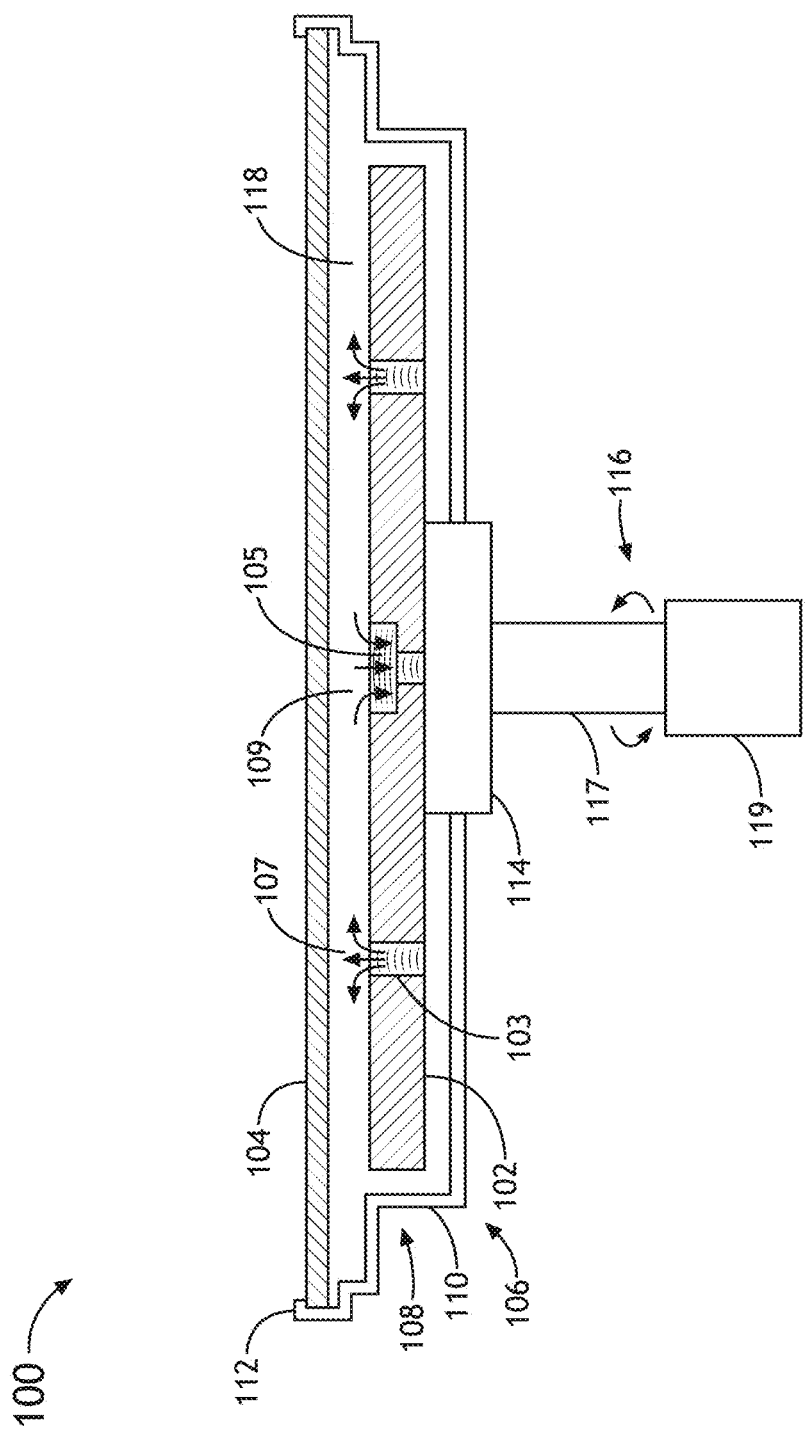
FIG. 1A is a cross-sectional view of a non-contact wafer chucking system, in accordance with one embodiment of the present disclosure.

FIG. 1A illustrates a simplified cross-sectional view of a non-contact wafer chucking system 100, in accordance with one embodiment of the present disclosure. In one embodiment, the wafer chucking system 100 includes a wafer chuck 100 for securing a wafer 104 above the surface of the wafer chuck 102 without making contact with the wafer chuck 102. In another embodiment, the wafer chucking system 100 includes gripper assembly 106. In another embodiment, the wafer chucking system 100 includes a rotational drive unit 116. The rotational drive unit 116 is coupled to the wafer chuck 102 and configured to selectably rotate the wafer chuck 102, the gripper assembly 106 and the wafer 104 during a wafer scanning process.

Figure 1B:
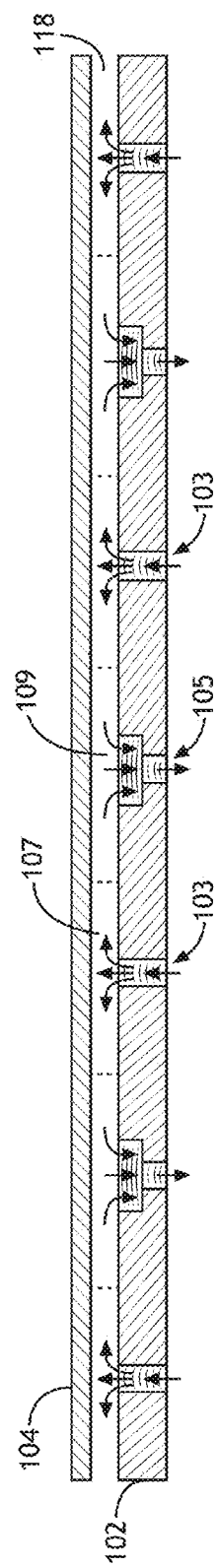
FIG. 1B is a cross-sectional view of a wafer chuck of a non-contact wafer chucking system, in accordance with one embodiment of the present disclosure.

In one embodiment, as shown in FIGS. 1A-1B, the wafer chuck 102 includes one or more pressurized gas elements 103. In one embodiment, a pressurized gas element 103 generates an associated pressurized region 107 at or near the output of the respective pressurized gas element 103. The pressurized region 107 serves to provide an upward force on the wafer 104. In this regard, the one or one or more pressurized gas elements 103 may generate one or more pressurized gas regions 107 across a surface of the wafer chuck 102 suitable for elevating the wafer 104 above the surface of the wafer chuck 102. In one embodiment, the wafer chuck 102 may include a plurality of pressurized gas elements 103, as depicted in FIG. 1B. In this regard, the plurality of pressurized gas elements 103 may generate one or more pressurized gas regions 107 distributed across the surface of the wafer chuck suitable for elevating the wafer 104 above the surface of the wafer chuck 102. It is noted herein that the pressurized gas regions 107 are not necessarily formed in a one-to-one correspondence with the pressurized gas elements 103. For example, two or more gas elements 103 (e.g., gas nozzles, gas channels, multiple gas nozzles, multiple gas channels) may contribute to form a single pressurized gas region 107.

In one embodiment, the one or more pressurized elements 103 of the wafer chuck 102 form a pressurized air pocket for elevating the wafer 104 above the surface of the wafer chuck 102. In this regard, the one or more pressurized elements 103 may form one or more pressurized air pockets (or other gas), which exerts a net upward force on the bottom of the wafer 104, thereby causing the wafer 104 to stabilize vertically at some location above the wafer chuck 104.

In another embodiment, as shown in FIGS. 1A-B, the wafer chuck 102 includes one or more vacuum elements 105. In one embodiment, a vacuum element 105 generates an associated reduced pressure, or vacuum, region 109 at or near the input of the respective vacuum gas element 105. For example, the one or more reduced pressure regions 109 may have a pressure that is lower than the one or more pressurized regions 107. The one or more vacuum elements 105 may generate one or more reduced pressure regions 109 across a surface of the wafer chuck 102 suitable for securing the wafer 104 above the surface of the wafer chuck 102 without contact taking place between the wafer 104 and the wafer chuck 102. In this regard, the reduced pressure regions 109 serve to provide a downward force on the wafer 104. The combination of the downward forced from the vacuum elements 105 and the upward force from the one or more pressurized gas elements serves to stabilize the vertical position of the wafer 102 at some location above the wafer chuck 102.

In one embodiment, the wafer chuck 102 may include a plurality of vacuum elements 105, as depicted in FIG. 1B. In this regard, the plurality of vacuum elements 105 may generate one or more reduced pressure regions 109 distributed across the surface of the wafer chuck 102 suitable for securing the wafer 104 above the surface of the wafer chuck 102. It is noted herein that the reduced pressure regions 109 are not necessarily formed in a one-to-one correspondence with the vacuum elements 105. For example, two or more vacuum elements 105 may contribute to form a single reduced pressure region 109. It is further noted herein that some amount of "cross-flow" may exist between the pressurized gas regions 107 and the reduced pressure regions 109. In this regard, gas from the pressurize gas elements 103 associated with regions 107 may flow to the reduced pressure regions 109 and be evacuated by the vacuum elements 105.

In one embodiment, the one or more pressurized gas elements 103 include one or more gas nozzles. For example, the one or more pressurized gas elements 103 may include, but are not limited to, one or more gas nozzles configured to direct gas (e.g., air) upward from the surface of the wafer chuck 104 in order to generate the one or more pressurized regions 10. For instance, a pressurized gas nozzle may include, but is not limited to, a bore hole machined out of the surface (or molded/cast into the surface) of the wafer chuck 102, with one or more gas delivery lines fluidically coupled to the hole, which serve to deliver gas (e.g., air) to the hole.

In one embodiment, the one or more pressurized gas elements 103 include one or more gas channels. For example, the one or more pressurized gas elements 103 may include, but are not limited to, one or more gas channels configured to direct gas (e.g., air) upward from the surface of the wafer chuck 104 in order to generate the one or more pressurized regions 107. For instance, a pressurized gas channel may include, but is not limited to, a recessed region machined out of the surface of the wafer chuck 102, with one or more gas delivery lines fluidically coupled to the recess, which serve to deliver gas (e.g., air) to the recessed channel.

In one embodiment, the one or more vacuum elements 105 include one or more gas nozzles. For example, the one or more vacuum elements 105 may include, but are not limited to, one or more gas nozzles configured to evacuate gas (e.g., air) downward from the surface of the wafer chuck 104 in order to generate the one or more reduced pressure regions 109. For instance, a vacuum nozzle may include, but is not limited to, a bore hole machined out of the surface (or molded/cast into the surface) of the wafer chuck 102, with one or more gas delivery lines fluidically coupled to the hole, which serve to evacuate gas (e.g., air) from the region near the hole.

In one embodiment, the one or more vacuum elements 105 include one or more gas channels. For example, the one or more vacuum elements 105 may include, but are not limited to, one or more gas channels configured to evacuate gas (e.g., air) downward from the surface of the wafer chuck 104 in order to generate the one or more reduced pressure regions 109. For instance, a vacuum gas channel may include, but is not limited to, a recessed region machined out of the surface of the wafer chuck 102, with gas delivery lines fluidically coupled to the recess, which serve to evacuate gas (e.g., air) from the region near the recessed channel.

In one embodiment, as shown in FIG. 1B, at least a portion of the vacuum elements 105 are interleaved with a portion pressurized gas elements 103. In this regard, one or more vacuum elements 105 may be arranged so as to alternate with one or more of the pressurized gas elements 103. It is recognized herein that the pressurized gas elements 103 and the vacuum gas elements 105 may be arranged in any pattern across the surface of the wafer chuck 102. For example, the pressurized gas elements 103 and the vacuum gas element 105 may be arranged in any geometric pattern (or patterns) known in the art.

For instance, the pressurized gas elements 103 and the vacuum gas elements 105 may be arranged in a linear grid, where one or more vacuum elements 105 are alternated, as function of X-Y position, with one or more pressurized gas elements 103. In another instance, the pressurized gas elements 103 and the vacuum gas elements 105 may be arranged in a circular grid, where one or more vacuum gas elements 105 are alternated, as a function of angular position about the wafer chuck 102, with the one or more pressurized gas elements 103. In another instance, the pressurized gas elements 103 and the vacuum elements 105 may be arranged in a concentric radial grid, where concentric rings of one or more vacuum gas elements 105 are alternated, as a function of radial position on the wafer chuck 102, with concentric rings of one or more pressurized gas elements 103.

Figure 1C:
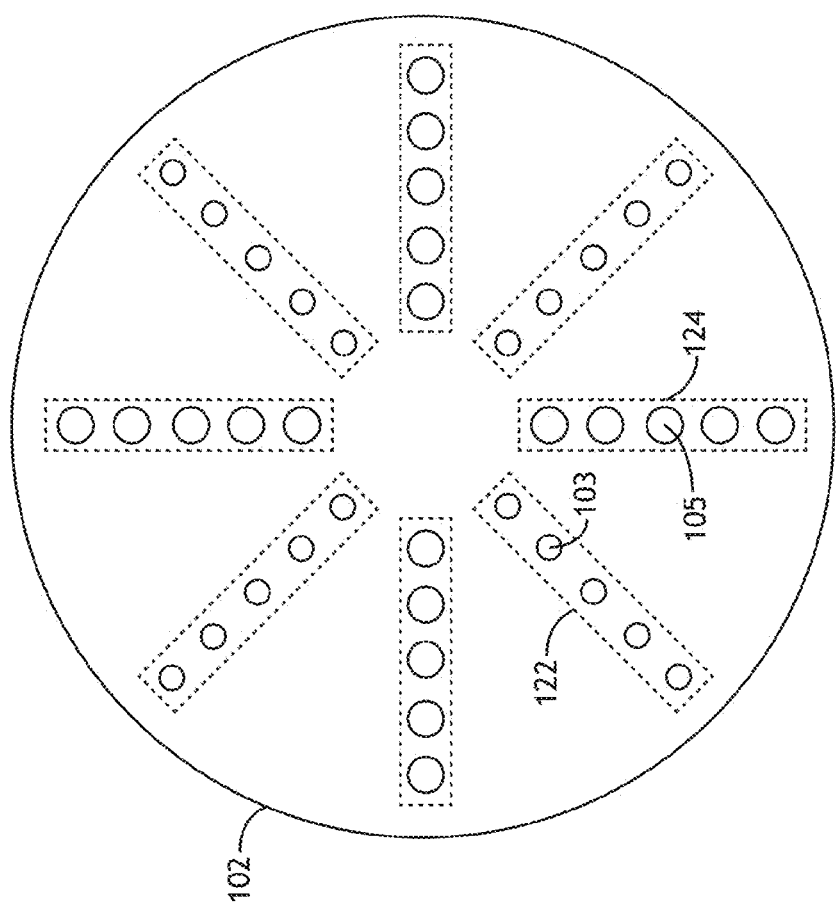
FIG. 1C is a top view of a wafer chuck of a non-contact wafer chucking system, in accordance with one embodiment of the present disclosure.

FIG. 1C illustrates an arrangement of pressurized gas elements 103 and vacuum elements 105, in accordance with one embodiment of the present disclosure. In one embodiment, the wafer chuck 102 includes multiple sets 122 of pressurized gas elements 103. In another embodiment, the wafer chuck 102 includes multiple sets 124 of vacuum gas elements 105. As shown in FIG. 1C, the sets 122 of pressurized gas elements 103 may be interleaved with the sets 124 of vacuum elements 105. It is noted herein that the arrangement depicted in FIG. 1C is not limiting and is provided merely for illustrative purposes. It is again recognized that the pressurized gas elements (or sets of pressurized gas elements) and the vacuum elements (or sets of pressurized gas elements) may be arranged across the surface of the wafer chuck in any suitable pattern.

It is noted herein that the one or more pressurized gas elements 103 may be in fluidic communication with a gas delivery system and/or network (not shown). In this regard, a gas source may be coupled to the delivery system/network, with gas being delivered to the pressurized gas elements 103 via the delivery system/network. In one embodiment, the delivery system/network may include one or more gas pumps for pumping gas, such as air, to the pressurized gas elements 103. In another embodiment, the delivery system/network may include one or more gas filters, such as an air filter, in order to filter the given gas prior to it being outputted through the pressurized gas elements 103. It is further noted herein that the one or more vacuum elements 105 may be in fluidic communication with a vacuum system and/or network (not shown). In this regard, a gas pump may be fluidically coupled to the vacuum elements 105 and configured to evacuate gas through the vacuum elements 105 and to an external reservoir (e.g., gas container, ambient atmosphere and the like). Those skilled in the art should recognize that there are a variety of gas delivery and gas vacuum mechanisms suitable for implementation in the system 100 of the present disclosure.

Figure 1D:
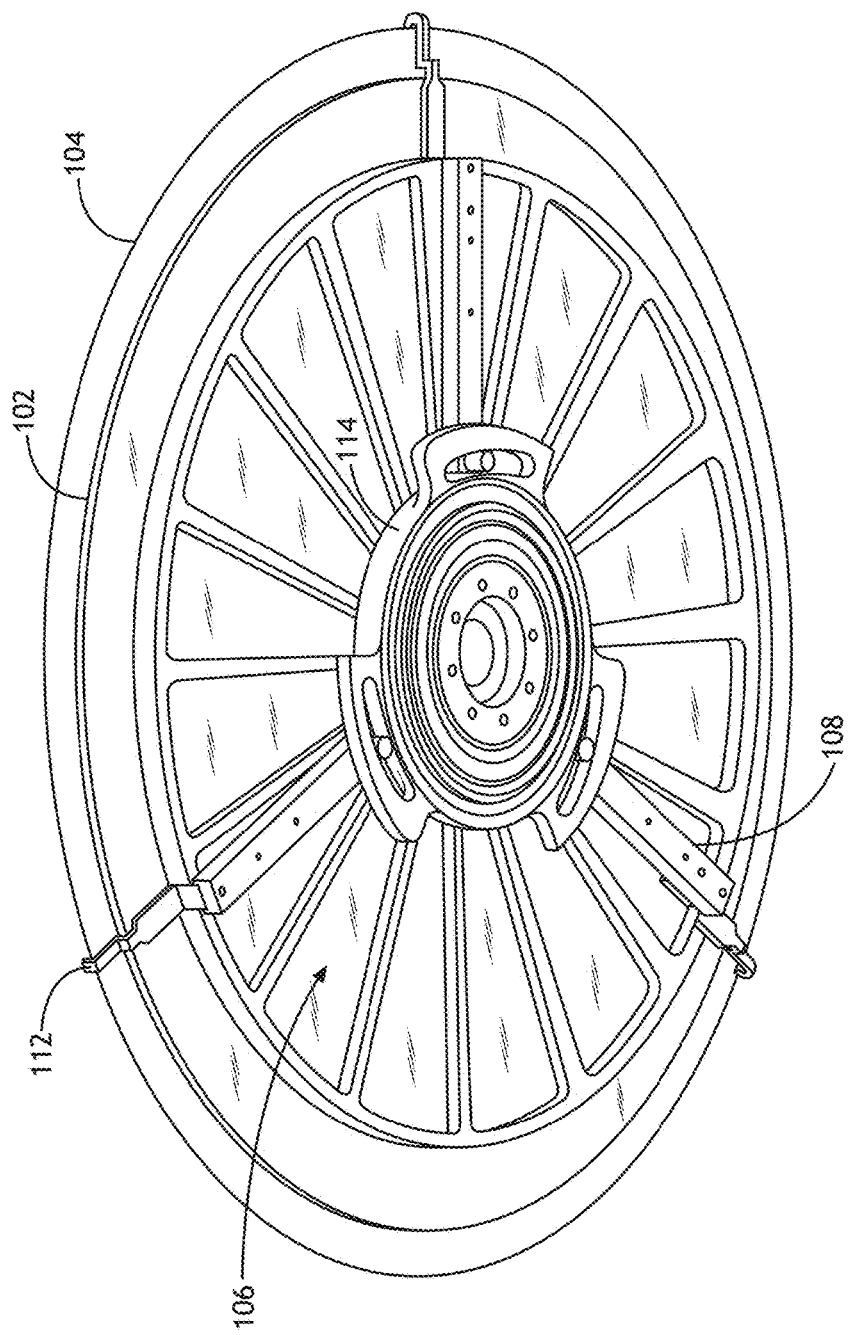
FIG. 1D is a schematic bottom view of a non-contact wafer chucking system, in accordance with one embodiment of the present disclosure.
Figure 1E:
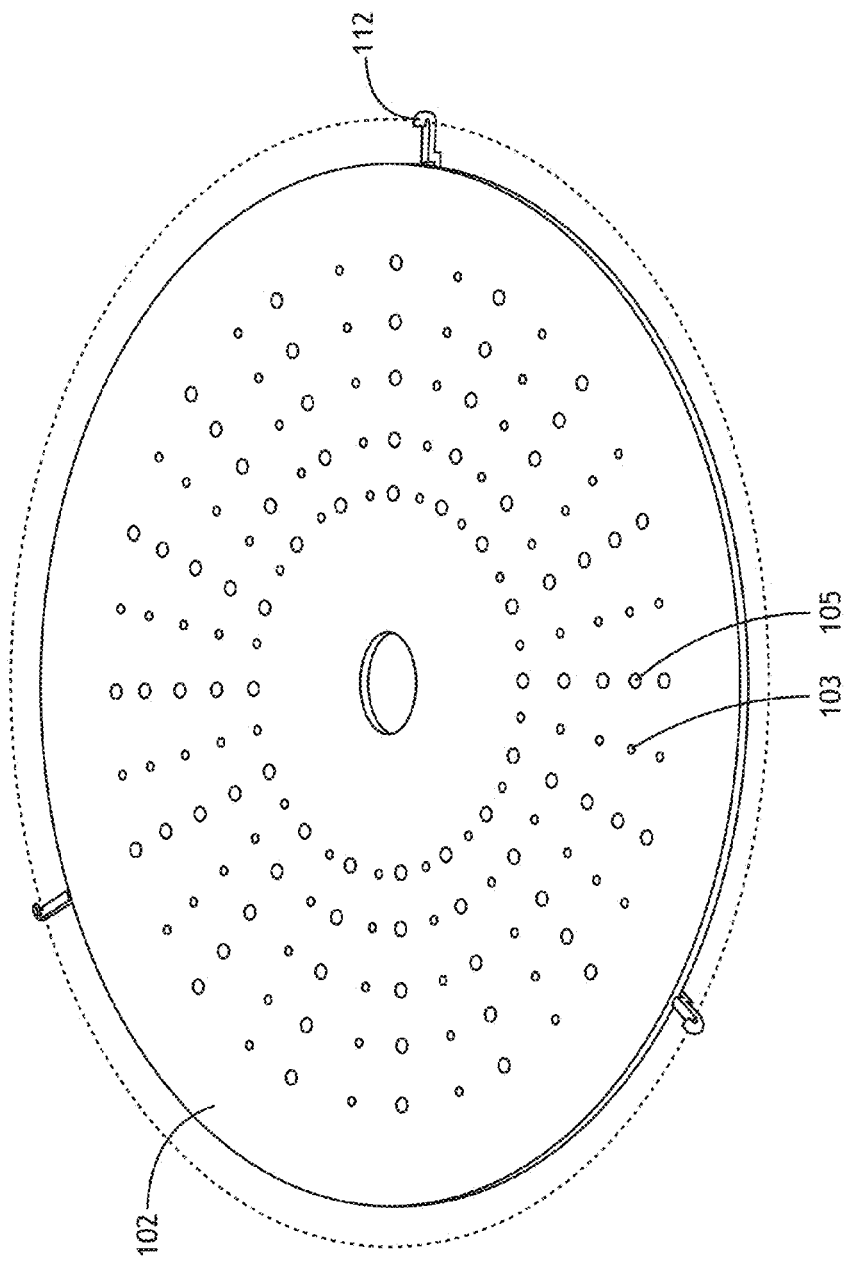
FIG. 1E is a schematic top view of a non-contact wafer chucking system, in accordance with one embodiment of the present disclosure.

FIG. 1D illustrates a schematic bottom view of the wafer chuck 102 and gripper assembly 106, in accordance with one or more embodiments of the present disclosure. As shown in FIG. 1D, the gripper elements 108 of the gripper assembly 106 act to laterally secure the wafer 104. Further, the cam unit 114 is mechanically coupled to the wafer chuck 102 and is used to drive the motion of the gripper elements 108 in securing the wafer 104. Once secure, the gripper elements of the gripper assembly 106 rotate the wafer 104 synchronously with the wafer chuck 102 as the wafer chuck 102 is rotated by the rotation drive unit 114 (not shown in FIG. 1D). FIG. 1E illustrates a schematic top view of the wafer chuck 102 securing the wafer 104, in accordance with one or more embodiments of the present disclosure. As shown in FIG. 1E, the wafer chuck 102 may include a set rows, aligned radially, of pressurized gas elements 103. In addition, the wafer chuck 102 may include a set of rows, aligned radially, of vacuum elements 105.

Referring again to FIG. 1A, in one embodiment, the gripper assembly 106 is mechanically coupled to a portion the wafer chuck 102. In one embodiment, the gripper assembly 106 is reversibly couplable to one or more edge portions of the wafer 104. In this regard, the gripper assembly 106 may laterally secure the wafer 104. For example, as shown in FIG. 1A, the gripper assembly 106 may serve to secure the wafer 104 along the horizontal direction without applying a significant contact force in the vertical direction. In another embodiment, the gripper assembly 106 may laterally and rotationally secure (relative to the wafer chuck 102) the wafer 104 such that when the wafer chuck 102 and the gripper assembly 106 are rotated by the rotational drive unit 116 the wafer 104 is also rotated. In this regard, while the wafer 104 rotates relative to an outside reference frame, the wafer 104 does not move significantly with respect to the surface of the wafer chuck 102 during a wafer scanning process.

In another embodiment, the gripper assembly 106 may serve to adjust the lateral position of the wafer 104 in order to substantially center the wafer 104 prior to rotation of the wafer 104 during a scanning process.

In one embodiment, the gripper assembly 106 of the wafer chucking system 100 includes one or more gripper elements 108. In another embodiment, the gripper elements 108 of the gripper assembly 106 include one or more connection arms, or rods, 110 and one or more gripper heads 112. In another embodiment, the one or more gripper heads 112 may include any mechanism known in the art suitable for securing the wafer 104. For example, the one or more gripper heads 112 may include, but is not limited to, a spring loaded device for securing the wafer. By way of another example, the one or more gripper heads 112 may include, but is not limited to, a frictional portion configured to secure the wafer 104 via friction.

In one embodiment, the gripper assembly 106 may include, but is not limited to, two or more gripper elements 108 (e.g., 2, 3, 4, 5 and so on). For example, as shown in FIGS. 1D and 1E, the gripper assembly 106 may include three gripper elements 108. In another instance, although not shown, the gripper assembly 106 may include four gripper elements 108.

Figure 1F:
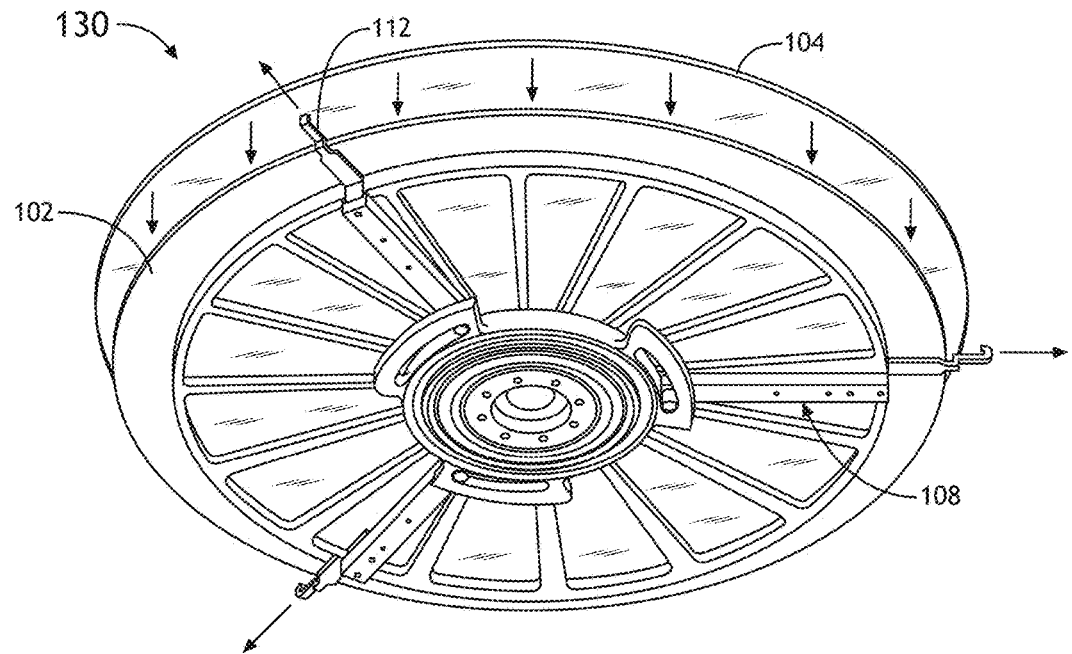
FIG. 1F is a schematic bottom view of a non-contact wafer chucking system having a gripper assembly in a disengaged state, in accordance with one embodiment of the present disclosure.
Figure 1G:
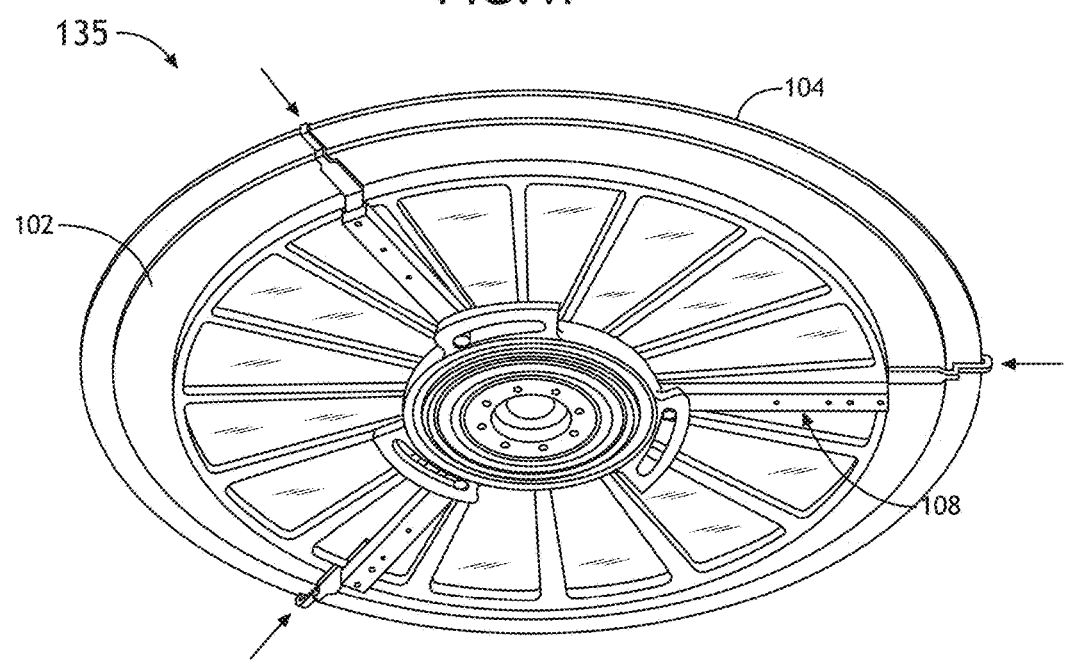
FIG. 1G is a schematic bottom view of a non-contact wafer chucking system having a gripper assembly in an engaged state, in accordance with one embodiment of the present disclosure.

In another embodiment, the gripper assembly 106 includes a cam unit 114. In one embodiment, the cam unit 114 is mechanically coupled to the gripper assembly 106. In one embodiment, as shown in FIGS. 1F and 1G, the cam unit is configured to drive the linear motion of one or more gripper elements 108 of the gripper assembly 106. In this regard, the cam unit 114 may selectably engage and/or disengage the gripper elements 108 with one or more portions of the wafer 104. For example, as shown in FIG. 1F, the cam unit 114 may cause the gripper elements 108 to move into an expanded, or disengaged, state. Such a configuration allows for a user (or robotic arm) to load a wafer 104 onto the wafer chuck 102 prior to a rotational scanning process. In addition, the cam unit 114 may be placed in a disengaged state when the user or robotic arm (not shown) unloads the wafer 104 from the chuck 102. By way of further example, as shown in FIG. 1G, the cam unit 114 may cause the gripper elements 108 to move into a retracted, or engaged state. Such a configuration serves to laterally secure the wafer 102, while the chuck 102 secures the wafer above the chuck 102, during a rotational scanning process.

Referring again to FIG. 1A, the wafer chuck 102 (and the connected gripper assembly 106) are supported by a shaft 116, or spindle, of the rotational drive unit 117. For example, the shaft 117 may be connected to a motor 119. In this regard, the motor 119 may be configured to rotate the shaft 117 at a selected rotational velocity, thereby rotating the wafer chuck 102, the gripper assembly 106 and the wafer 104 about an axis perpendicular to the surface of the wafer chuck 102. For instance, the wafer chuck 102, the gripper assembly 106 and the wafer 104 may be rotated at speeds greater than 1,000 revolutions per minute (rpm) (e.g., 1,000 to 10,000 rpm).

Figure 2A:
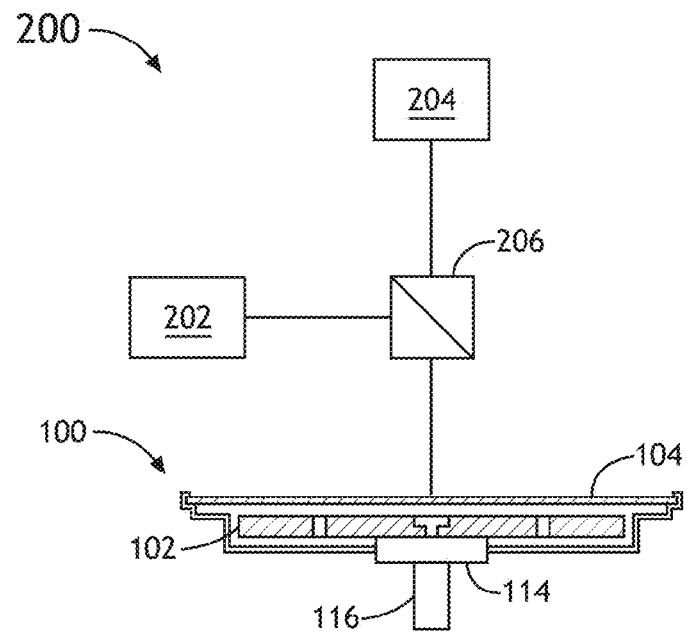
FIG. 2A is a simplified schematic view of a wafer inspection system equipped with a non-contact wafer chucking system, in accordance with one embodiment of the present disclosure.
Figure 2B:
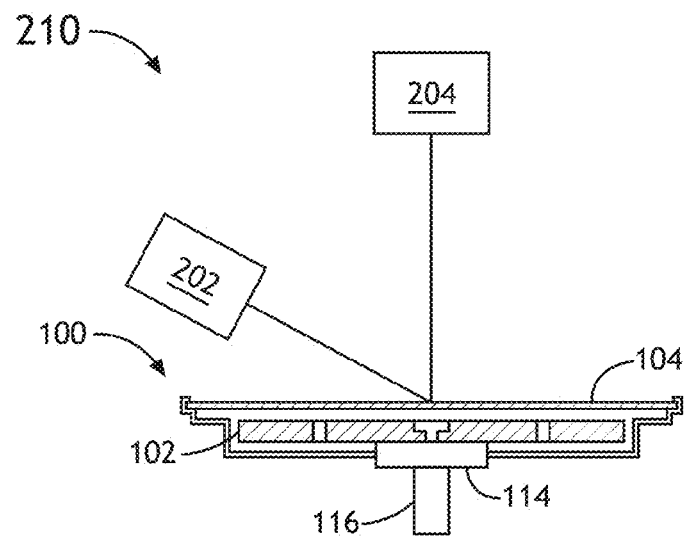
FIG. 2B is a simplified schematic view of a wafer inspection system equipped with a non-contact wafer chucking system, in accordance with one embodiment of the present disclosure.

FIGS. 2A and 2B illustrate high-level block diagram views of inspection systems 200, 210 equipped with the non-contact wafer chucking system 100, in accordance with one or more embodiments of the present disclosure. In one embodiment, the wafer inspection systems 200, 210 of the present disclosure may include the non-contact wafer chucking system 100, as described previously herein. In one embodiment, the inspection systems 200, 210 further include least one light source 202 (e.g., one or more lasers, one or more broadband light sources and etc.) configured to illuminate an area on the surface of the wafer 104. In another embodiment, the inspection systems 200, 210 include one or more detectors 204, or cameras, suitable for detecting light reflected, diffracted or scattered from the area illuminated by the light source 202. In one embodiment, the one or more detectors 204 may include, but are not limited to, a CCD or TDI-CCD detector, or a photomultiplier detector. In addition, the inspection systems 200, 210 may include a set of optical elements (e.g., illumination optics, collection optics, beam splitters 206, filters and the like) configured for directing (and focusing) illumination from the light source 202 onto the surface of the wafer 104 and, in turn, directing illumination from the surface of the wafer 104 to the imaging portion of the detector 204 of the inspection systems 200, 210. For instance, the set of optical elements for the systems 200, 210 may include, but is not limited to, a primary imaging lens suitable for imaging the illuminated area of the wafer onto a collection portion(s) of the detector 204. Further, the imaging detector 204 may be communicatively coupled to an image processing computer which may identify and store imagery data acquired from the detector 204.

The inspection systems 200, 210 of the present disclosure may be configured as any inspection system known in the art. For example, as shown in FIG. 2A, the inspection system 200 of the present invention may be configured as a bright field (BF) inspection system. Alternatively, as shown in FIG. 2B, the inspection system 210 may be configured as a dark field (DF) inspection system. Applicant notes that the optical configurations depicted in FIGS. 2A and 2B are provided merely for illustrative purposes and should not be interpreted as limiting. In a general sense, the inspection systems 200, 210 of the present disclosure may include any set of imaging and optical elements suitable for imaging the surface of the wafer 104. Examples of wafer inspection tools are described in detail in U.S. Pat. No. 7,092,082, U.S. Pat. No. 6,702,302, U.S. Pat. No. 6,621,570 and U.S. Pat. No. 5,805,278, which are each herein incorporated by reference.

Figure 3:
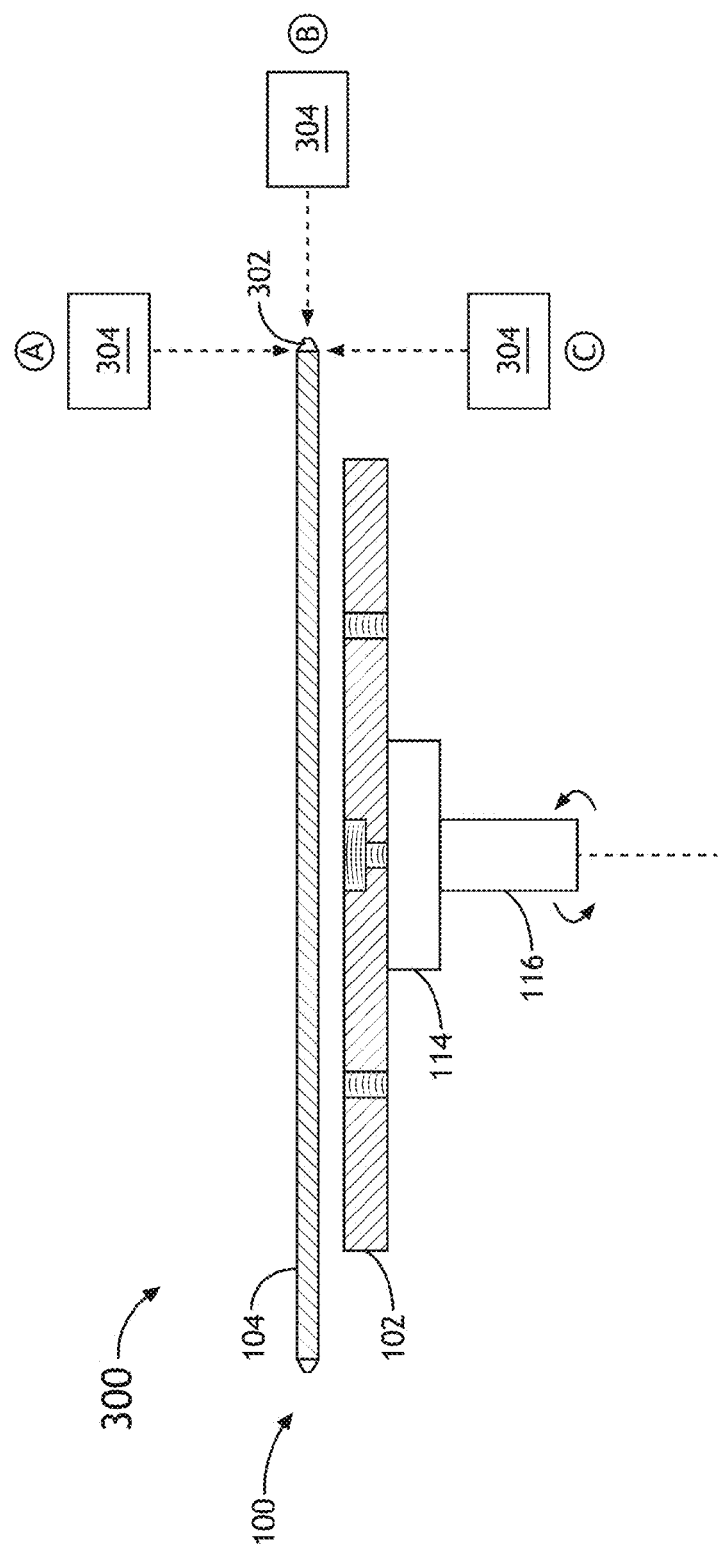
FIG. 3 is a simplified schematic view of a wafer edge inspection system equipped with a non-contact wafer chucking system, in accordance with one embodiment of the present disclosure.

FIG. 3 illustrate high-level block diagram views of an edge inspection 300 equipped with the non-contact wafer chucking system 100, in accordance with one or more embodiments of the present disclosure. For purposes of clarity, the gripper assembly 106 is not depicted in FIG. 3, even though it is recognized herein that the gripper assembly 106 is present in such an edge inspection setting. As shown in FIG. 3, an edge inspection system 300 may include a detector 304 suitable for collecting imagery data from the edge region 302 of the wafer 104. It is further recognized that the inspection system 300 allows for various portions of the edge 302 to be inspected using the detector 304. For example, as shown in FIG. 3, the detector 304 may collect imagery data at a location A at the top portion of the edge 302 of the wafer 104 (e.g., top portion of wafer bevel). By way of another example, as shown in FIG. 3, the detector 304 may collect imagery data at a location B at the center portion of the edge 302 of the wafer 104 (e.g., center of wafer bevel). By way of another example, as shown in FIG. 3, the detector 304 may collect imagery data at a location C at the bottom portion of the edge 302 of the wafer 104 (e.g., bottom portion of wafer bevel).

Figure 4:
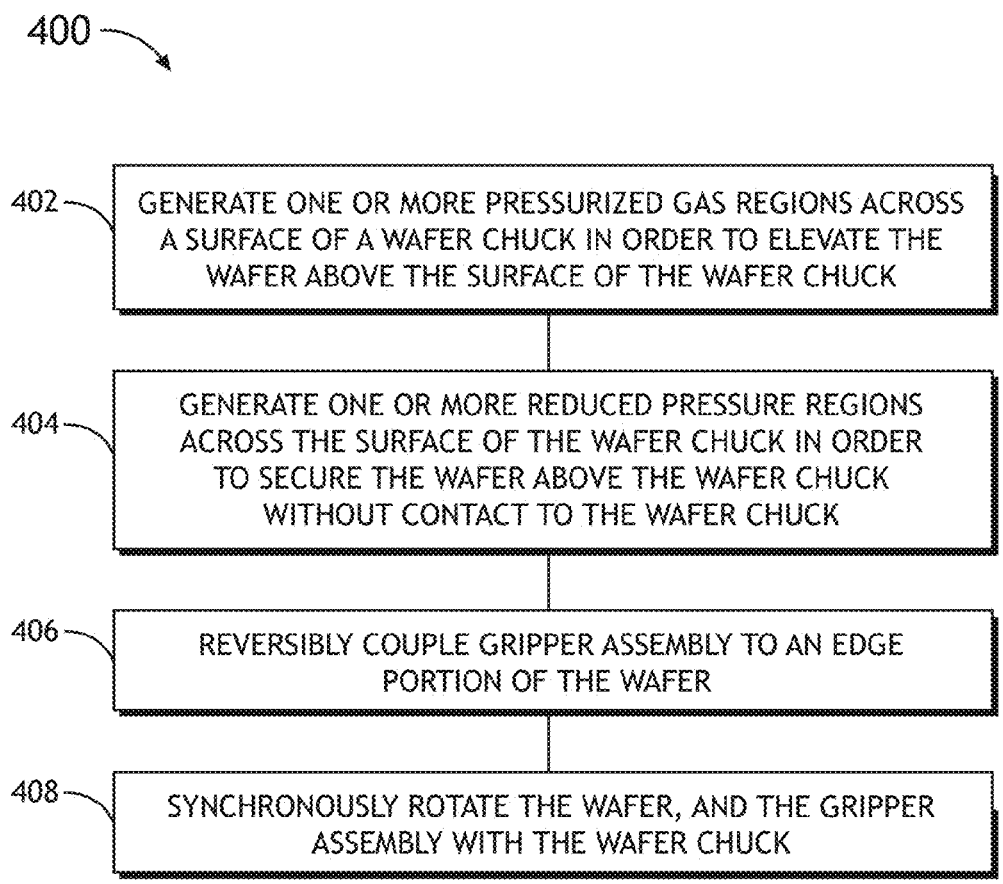
FIG. 4 is flow diagram of depicting a method for non-contact chucking of a wafer, in accordance with one embodiment of the present disclosure.

FIG. 4 illustrates a flow diagram depicting the steps of a method 400 for non-contact chucking of a wafer, in accordance with one or more embodiments of the present disclosure. In step 402, one or more pressurized gas regions are generated across a surface of a wafer chuck in order to elevate the wafer above the surface of the wafer chuck. In step 404, one or more reduced pressure regions are generated across the surface of the wafer chuck in order to secure the wafer above the wafer chuck without contact to the wafer chuck. In step 406, one or more gripper elements are reversibly coupled, or attached, to an edge portion of the wafer in order to rotationally secure the wafer with respect to the wafer chuck. In step 408, the wafer, the plurality of gripper elements and the wafer chuck are synchronously rotated at a selected rotational velocity.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. An apparatus for non-contact chucking of a wafer comprising:
   a wafer chuck, the wafer chuck including one or more pressurized gas elements configured to generate one or more pressurized gas regions across a surface of the wafer chuck suitable for elevating the wafer above the surface of the wafer chuck, the wafer chuck further including one or more vacuum elements configured to generate one or more reduced pressure regions across the surface of the wafer chuck, the reduced pressure regions having a pressure lower than the pressurized gas regions, the one or more reduced pressure regions suitable for securing the wafer above the wafer chuck without contact to the wafer chuck;
   a gripper assembly coupled to a portion of the wafer chuck, wherein the gripper assembly includes a plurality of gripper elements; and
   a rotational drive unit mechanically coupled to the wafer chuck,
   wherein the rotational drive unit is configured to selectively rotate the wafer chuck,
   wherein the gripper assembly includes a cam unit configured to drive one or more of the gripper elements along a radial direction of the wafer chuck so as to selectably engage the gripper assembly with one or more edge portions of the wafer so as to secure the wafer such that the wafer and the gripper assembly rotate synchronously with the wafer chuck during rotation of the wafer chuck by the rotational drive unit.

2. The apparatus of claim 1, wherein the one or more pressurized gas elements comprise:
   one or more pressurized gas nozzles configured to direct gas upward from the surface of the wafer chuck in order to generate the one or more pressurized regions.

3. The apparatus of claim 1, wherein the one or more pressurized gas elements comprise:
   one or more pressurized gas channels configured to direct gas upward from the surface of the wafer chuck in order to generate the one or more pressurized regions.

4. The apparatus of claim 1, wherein the one or more pressurized elements of the wafer chuck form a pressurized air pocket for elevating the wafer above the surface of the wafer chuck.

5. The apparatus of claim 1, wherein the one or more vacuum elements comprise:
   one or more vacuum nozzles configured to evacuate gas from the surface of the wafer chuck in order to generate the one or more reduced pressure regions.

6. The apparatus of claim 1, wherein the one or more vacuum elements comprise:
   one or more vacuum channels configured to evacuate gas from the surface of the wafer chuck in order to generate the one or more reduced pressure regions.

7. The apparatus of claim 1, wherein the one or more pressurized gas elements comprise:
   a plurality of pressurized gas elements.

8. The apparatus of claim 7, wherein the one or more vacuum elements comprise:
   a plurality of vacuum elements.

9. The apparatus of claim 8, wherein at least some of the plurality of vacuum elements are interleaved with at least some of the plurality of pressurized gas elements.

10. The apparatus of claim 1, wherein the one or more pressurized gas elements comprise:
    a plurality of sets of pressurized gas elements.

11. The apparatus of claim 10, wherein the one or more vacuum elements comprise:
a plurality of sets of vacuum elements.

12. The apparatus of claim 11, wherein at least some of the plurality of sets of vacuum elements are interleaved with at least some of the plurality of sets of pressurized gas elements.

13. The apparatus of claim 1, wherein the one or more pressurized regions are proximate to the one or more reduced pressure regions.

14. The apparatus of claim 1, wherein the one or more pressurized regions are adjacent to the one or more reduced pressure regions.

15. The apparatus of claim 1, wherein the one or more pressurized regions alternate with the one or more reduced pressure regions.

16. The apparatus of claim 1, wherein the plurality of gripper elements comprises:
three or more gripper elements.

17. The apparatus of claim 1, wherein at least some of the gripper elements are couplable to an edge portion of the wafer.

18. The apparatus of claim 1, wherein the gripper assembly is configured to selectably disengage from the edge portion of the wafer.

19. The apparatus of claim 1, wherein the gripper assembly is configured to laterally position the wafer on the wafer chuck.

20. The apparatus of claim 1, wherein the rotational drive unit comprises:
a spindle; and
a motor.

21. The apparatus of claim 1, wherein the wafer comprises:
a semiconductor wafer.

22. An optical system comprising:
a wafer chucking sub-system including:
a wafer chuck, the wafer chuck including one or more pressurized gas elements configured to generate one or more pressurized gas regions across a surface of the wafer chuck suitable for elevating the wafer above the surface of the wafer chuck, the wafer chuck further including one or more vacuum elements configured to generate one or more reduced pressure regions across the surface of the wafer chuck, the reduced pressure regions having a pressure lower than the pressurized gas regions, the one or more reduced pressure regions suitable for securing the wafer above the wafer chuck without contact to the wafer chuck;
a gripper assembly coupled to a portion of the wafer chuck, wherein the gripper assembly includes a plurality of gripper elements; and
a rotational drive unit mechanically coupled to the wafer chuck, wherein the rotational drive unit is configured to selectively rotate the wafer chuck, wherein the gripper assembly includes a cam unit configured to drive one or more of the gripper elements along a radial direction of the wafer chuck so as to selectably engage the gripper assembly with one or more edge portions of the wafer so as to secure the wafer such that the wafer and the gripper assembly rotate synchronously with the wafer chuck during rotation of the wafer chuck by the rotational drive unit; and
an illumination source configured to illuminate one or more portions of the wafer secured by the wafer chucking sub-system; and
a detector configured to collect illumination from the illuminated one or more portions of the wafer.

23. The optical system of claim 22, wherein the optical system is configured as an inspection tool.

24. The optical system of claim 22, wherein the optical system is configured as a wafer edge inspection tool.

25. The optical system of claim 23, wherein the optical system is configured as at least one of a brightfield inspection tool or a darkfield inspection tool.

26. The optical system of claim 22, wherein the optical system is configured as a metrology tool.

27. The optical system of claim 22, wherein the one or more pressurized gas elements comprise:
one or more pressurized gas nozzles configured to direct gas upward from the surface of the wafer chuck in order to generate the one or more pressurized regions.

28. The optical system of claim 22, wherein the one or more pressurized gas elements comprise:
one or more pressurized gas channels configured to direct gas upward from the surface of the wafer chuck in order to generate the one or more pressurized regions.

29. The optical system of claim 22, wherein the one or more vacuum elements comprise:
one or more vacuum nozzles configured to evacuate gas from the surface of the wafer chuck in order to generate the one or more reduced pressure regions.

30. The optical system of claim 22, wherein the one or more vacuum elements comprise:
one or more vacuum channels configured to evacuate gas from the surface of the wafer chuck in order to generate the one or more reduced pressure regions.

31. The optical system of claim 22, wherein the one or more pressurized gas elements comprise:
a plurality of pressurized gas elements.

32. The optical system of claim 22, wherein the one or more vacuum elements comprise:
a plurality of vacuum elements.

33. The optical system of claim 22, wherein the plurality of gripper elements comprises:
three or more gripper elements.

34. The optical system of claim 22, wherein at least some of the gripper elements are couplable to an edge portion of the wafer.

35. The optical system of claim 22, wherein the gripper assembly is configured to selectably disengage from the edge portion of the wafer.

36. The optical system of claim 22, wherein the gripper assembly is configured to laterally position the wafer on the wafer chuck.

37. A method for non-contact chucking of a wafer comprising:
generating one or more pressurized gas regions across a surface of a wafer chuck in order to elevate the wafer above the surface of the wafer chuck;
generating one or more reduced pressure regions across the surface of the wafer chuck in order to secure the wafer above the wafer chuck without contact to the wafer chuck;
driving one or more gripper elements of a gripper assembly along a radial direction of the wafer chuck so as to selectably engage the gripper assembly with one or more edge portions of the wafer so as to secure the wafer; and
synchronously rotating the wafer, gripper assembly and the wafer chuck at a selected rotational velocity.

* * * * *